Figure 1:

United States Patent [19]
Jakobsson

[11] Patent Number: 5,771,903
[45] Date of Patent: Jun. 30, 1998

[54] SURGICAL METHOD FOR REDUCING THE FOOD INTAKE OF A PATIENT

[75] Inventor: Arne Jakobsson, Antibes, France

[73] Assignee: Kirk Promotions Limited, St. Johns, Isle of Man

[21] Appl. No.: 532,357

[22] Filed: Sep. 22, 1995

[51] Int. Cl.⁶ .................................................. A61B 19/00
[52] U.S. Cl. .......................... 128/898; 128/897; 606/151; 606/157; 606/213; 606/228
[58] Field of Search ................................ 606/151, 157, 606/213, 228; 128/897–898

[56] References Cited

U.S. PATENT DOCUMENTS 3,875,928  4/1975  Angelchik ............................. 128/898
4,592,339  6/1986  Kuzmak et al. ....................... 606/157
5,160,338  11/1992  Vincent ................................. 606/228

FOREIGN PATENT DOCUMENTS 906526  2/1982  U.S.S.R. ............................... 128/898

Primary Examiner—Jennifer Bahr
Assistant Examiner—Rosiland Kearney
Attorney, Agent, or Firm—Burns, Doane, Swecker & Mathis, L.L.P.

[57] ABSTRACT

The present invention provides a surgical method for reducing the food intake of a patient by dissecting the lower part of the Esophagus of a patient, applying a band to form a loop around the lower part of the Esophagus and displacing an upper part of the stomach through the loop, thereby forming a small pouch above the band wherein the final position of the band is above the Bursa Omentalis.

9 Claims, 2 Drawing Sheets

SURGICAL METHOD FOR REDUCING THE FOOD INTAKE OF A PATIENT

FIELD OF INVENTION

The invention relates to a surgical method for reducing the food intake of a patient by applying a band around the Esophagus to form a restriction and a small pouch of a portion of the stomach above said restriction. The invention also relates to a band for forming such a restriction and a small pouch and also the use of a band for this purpose. The device is mainly intended for reducing the food intake of a patient for achieving a weight reduction, but it could also be used for other purposes, e g Hernia.

PRIOR ART

In the early eighties overweight operations were carried out by placing a band around the stomach, which formed a restriction, thereby preventing food from passing downwards, or more correctly reducing the speed and the amount of food being eaten. After a few years of use of the new surgical method it became evident that it was very difficult to apply the band with an appropriate tightness—if the band was laid to tight around the stomach, patients were affected by vomiting attachs, on the contrary, if the band was too loose, the hole between the upper/lower part of the stomach became too large, resulting in the eating or the weight problems being unaffected. Unfortunately, therefore many operations were a failure.

The solution of this problem was to provide a band having an inflatable balloon on the inside thereof, like a blood pressure cuff, connected to an injection port so it became possible to change the inside diameter of the band after the operation. In that way, if people were vomiting after the operation it was possible to drain off some fluid through the injection port, thus reducing the opening of the band loop, thereby getting a larger restriction between the upper/lower part of the stomach. On the contrary, if patients did not lose weight, it was possible to inject a certain amount of fluid through the injection port, thereby narrowing the restriction between the upper/lower part of the stomach, the so called Stoma diameter. This operation was clearly better than the earlier method, but unfortunately this operation was not without problems. Namely, there existed two main difficulties:

The loop band appeared to have a tendency to dislocate downwards towards the lower part of the stomach. This was prevented by suturing the lower part of the stomach to the upper part of the stomach, so called tunnelling, to prevent the band from dislocating downwards the major curvature of the stomach. However, sometimes these sutures ruptured, thus negatively affecting a desired long term weight loss.

The second difficulty was that according to my researches, the upper part of the stomach rapidly increased in size, approximately ten times of its original size, with less weight reduction as a consequence.

The most frequently used surgical method during this period was vertical banded gastroplastic (VBG). In this operation a hole through both the back and front wall of the stomach were made with a two row suture instrument. With another suture instrument a four row steel suture was made from these holes up to the Hisca winkle. The smaller upper part of the stomach then functions as a prolongation of the Esophagus. After this step a band was inserted through the hole and applied around the minor side of the stomach, the ends of the band being sutured to each other to form a closed band loop. This operation is not reversible and in a large study made by Mason, United States, including more than a thousand patients, 14% of the patients required a re-operation. The weight reduction was acceptable but by no means satisfactory.

Normally, either the gastric band operation or the vertical band in the gastroplastic operation is performed, the Bursa Omentalis between the lower part of the stomach and the colon is opened. A hole in the Bursa omentalis is made under the stomach. It is then possible to operate from both sides of the stomach, both from the interior and the posterior side. In gastric banding two holes on the minor and major side of the stomach are made. In VBG wherein holes are made through both the back and front walls of the stomach, using a two row suture instrument, also penetration of Bursa Omentalis is required.

The upper part of the stomach wall is adherent to the underlying tissue. There is also a blood vessel—Gastrica Superior—quite high up, close to the stomach and coming up on the minor side of the stomach wall. Close to this blood vessel there is also a fibrotic band, Fascia Tissue—extending from the stomach to the liver. Therefore the band used for the gastric banding is placed just below this blood vessel and said fibrotic band over through the Fundus on the major side of the stomach. Because of the adherence of the stomach wall on the underside, the gastric band can not be localized higher up, when it is tightened around the stomach. Therefore, when this operation is carried out, the stomach portion situated above the band is pulled downwards under the band and the stomach wall under the band is sutured to the stomach wall above the band—thereby providing a tunnel for the band, preventing it from being dislocated downwardly and the same time making the size of the upper part of the stomach, the pouch volume, sufficiently small. If the stomach portion is not pulled downwardly, the pouch will be too large to be effective. But this measure also implies a pretensioning of the stomach portion, which results in said portion rapidly moving upwards, if the sutures rupture, with a too large pouch volume as a consequence.

Normally, according to my studies, the pouch volume initially often will become too large and it is an absolute necessity that the tunnelling sutures do not rupture, for maintaining the pouch volume in the long term. The main problem however, is that the pouch volume, even if the gastric band does not dislocate, rapidly increases in size during the first year after the operation. My studies show that the size of the upper gastric pouch in average increases ten times.

OBJECT OF THE INVENTION

The object of the invention is to propose a new surgical method for providing a restriction in the stomach with the use of a band, which will not dislocate and which method is less complicated, provides for a better long term result than the prior art, and permits that a very small pouch for the food could be shaped in a controlled manner.

This object is reached in accordance with the invention by the features defined in claim 1.

Another object of the invention is to provide a device to be used in association with said surgical method and which permits a controlled adjustment of said restriction as a function of an increase of the pouch volume. Said object is attained by the device defined in claim 7.

PREFERRED EMBODIMENT OF THE INVENTION

Figure 2:
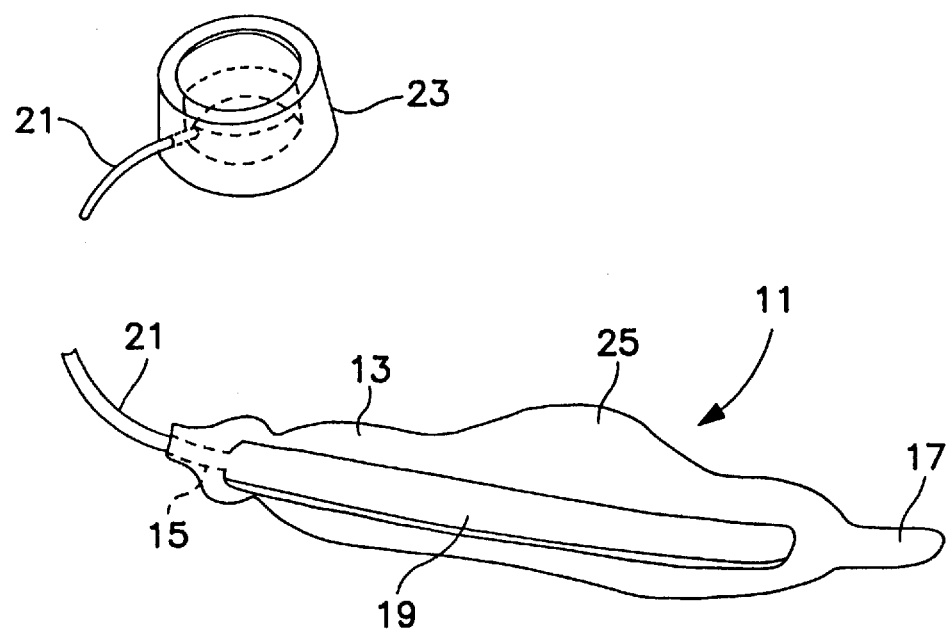

A preferred embodiment of the surgical method and of the device will now be explained by way of example with reference to the annexed drawings, wherein FIG. 1 is a perspective view which schematically shows the device of the invention applied on Esophagus after the operation, and FIG. 2 is a schematic perspective view of one embodiment of the device of the invention.

Contrary to the prior art, the Bursa Omentalis is not opened in my surgical method. After the penetration of the abdominal wall, the left lobe of the liver is released from the diaphragms muscle. In this area there is only a fibrotic connection without any blood vessels. Thus, it is an easy operation without any complications. After release of the left liver lobe, the lower part of the Esophagus 3 easily can be seen. The lower part of the Esophagus 3 is then released and a band 11 is then applied around the lower part of the Esophagus 3. The two ends of the band 11 are then sutured to each other to form a loop, the function of said loop will be explained later on. The most upper part of the anterior stomach 1 wall is pulled up inside the band loop and then the small part of the stomach 1 wall forming a pouch 5 above the band is sutured to the lower part of the stomach situated below the band 11, which is tunnellated by a row of sutures 7 at the anterior wall. The band 11 has now obtained a very stable position, resting on the posterior part of the Esophagus 3, which due to the adherence of the upper part of the stomach 1 to the underlying tissue, itself is very stable in this area. Thus, there is no possiblity that the band 11 will dislocate downwardly. The most upper part of the anterior stomach wall being pulled through the band and the tunnelling sutures 7 being made, the posterior part of the band 11 will be situated around the Esophagus 3 and the anterior part of the band will be placed less than 1 cm below Cardia.

The advantages of the surgical method in accordance with the invention are mainly:

1. The band 11 has a very stable position and there is no risk for further dislocation thereof downwards towards the stomach 1, which provides a warranty for good long term results.

2. The tunnelling sutures 7 are not critical for achieving good results with this method. They only facilitate in the beginning the expansion of the very small food pouch 5.

3. The surgical method is much easier with less risks and less operating time than in the prior art.

4. A very small upper pouch 5 may be formed, which is an important feature, since the pouch will expand about ten times in size for the first years. A small pouch 5 volume predicts a good long term result.

5. The method allows for a wide range of adjustment of the Stoma diameter, so that the Stoma opening may be decreased during a long period of time concurrently with the expansion of the pouch, in a manner that will be described herinafter.

The device of the invention will now be described.

Referring to FIG. 2, the device comprises a band 11, having a supporting elongated outer wall 13 of a substantially non expansible, and flexible material. Said wall is preferably made of a reinforced plastic material and has such a flexibility that it could be bent to form a closed loop. The ends 15, 17 of the outer wall 13, could be joined to each other, e g by suturing, a snap-lock connection or by any other suitable joint means.

The band has an inner wall 19 made of an expansible material, preferably an elastic, soft plastic material or the like. Said inner walls 19 are glued or heat-sealed to the outer wall 13, thereby providing an expansible cavity between the walls 13, 19. As an alternative an expansible tube might be connected (glued or heat-sealed) to the outer wall 13, the ends of said tube being sealed to define a closed expansible cavity. A conduit 21, e g a tube of silicone rubber, is provided, one end of which opens into the cavity, the other end of which opens into an injection port 23 for supplying or draining off fluid to or from, respectively, said cavity.

The inner wall of the band 19 may be inwardly expanded from adjacent the outer wall 13 to such an extent that when a band loop has been formed, the opening of the loop will be substantially obstructed. Preferably, when used in the above described surgical method the unexpanded loop has an inner diameter of approximately 35 mm.

The band may have a varying width along its main extension, thereby providing a support portion 25 with a greater area intended to rest against the Esophagus 3 portion. In this way the surface pressure against the Esophagus 3 wall will be reduced, thereby diminishing the stresses onto the Esophagus 3 wall.

The wide range of adjustment of the cavity or the inner wall 19 is a very important feature of the band for accomplishing a satisfying long term result of the method of the invention.

As described, initially, the band 11 loop is disposed around the Esophagus 3, whereupon the upper part of the stomach 1 is pulled up through the band loop and then sutured to the stomach 1 part situated below the restriction, thereby forming a pouch 5 having a very small volume, e.g. about 7 ml and tunnellating the band 11. If the loop were directly tightened to its final size in association with the operation, said volume would be too small to give the patient sufficient nutrition directly after the operation. However, the pouch 5 will expand in course of time, normally up to ten times of its original size after about a year. Therefore, in order to solve the malnutrition problems the opening of the loop is initially adjusted to have its maximum size just after the operation. As time goes, the pouch 5 will expand, thereby permitting a reduction of the loop opening without serious consequences for the patient. Said reduction is accomplished by injecting through the injection port 23 an appropriate amount of fluid into the cavity of the band loop. This adjustment must be carried out rather frequently in order to follow the expansion of the pouch 5. Therefore, the injection port 23 should be implanted in a easily accessible region. A suitable place is subcutaneously against the lower part of Sternum 8, which provides a support for the injection port 23 during the fluid injection steps.

At the end of the expansion of the pouch 5, say after about a year, the loop opening has been reduced to its final size. The total process has been completed with a smooth, stepwise reduction of the loop opening without appreciable problems for the patient.

It should be noted that the device could be varied in different ways. For example, the fluid might be a gas, but preferably it is a liquid, preferably an oil or an isotonic salt solution. It should further be evident that all components of the device are made of biocompatible materials.

I claim:

1. A surgical method for reducing the food intake of a patient, comprising, dissecting the lower part of the Esophagus of a patient, applying a band to form a loop around the Esophagus, displacing an upper part of the stomach through said loop, thereby forming a small pouch above said band connected to the Esophagus, and suturing said upper part to the stomach wall, thereby tunnelating said band.

2. A surgical method in accordance with claim 1, further comprising using a band having a wider portion than the rest of said band, said wider portion being disposed against the lower part of the Esophagus.

3. A surgical method in accordance with claim 1, further comprising the use of a band having an essentially nonexpansible outer wall and an expansible inner wall, said outer and inner walls being joined together to form a closed expansible cavity connected to said outer wall, a conduit being provided, one end of which opens into said cavity, the other end of which opens into an injection port.

4. A surgical method in accordance with claim 3, wherein said opening of said band loop is adjusted, or narrowed as a function of an expansion of said pouch.

5. A surgical method in accordance with claim 3 wherein said injection port is implanted subcutaneously preferably against the lower part of Sternum.

6. A surgical method in accordance with claim 1, wherein said pouch in the unexpanded condition has a volume of about 7 ml.

7. A surgical method comprising the steps of:
   dissecting the lower part of the Esophagus of a patient;
   applying a band to form a loop around the lower part of the Esophagus; and
   displacing an upper part of the stomach through said loop, thereby forming a small pouch above said band;
   wherein the final position of said band is above the Bursa Omentalis.

8. A surgical method comprising the steps of:
   dissecting the lower part of the Esophagus of a patient in such a way that a portion of the posterior surface of the stomach remains adherent to the underlying tissue;
   applying a band to for a loop around the lower part of the Esophagus; and
   displacing an upper part of the stomach through said loop, thereby forming a small pouch above said band;
   wherein the final position of said band is in the area where the lower part of the Esophagus and the upper part of the stomach is adherent to the underlying tissue.

9. A surgical method for reducing the food intake of a patient, comprising
   dissecting the lower part of the Esophagus of a patient,
   applying a band to form a loop around the Esophagus,
   displacing an upper part of the stomach through said loop, thereby forming a small pouch above said band connected to the Esophagus.

* * * * *

UNITED STATES PATENT AND TRADEMARK OFFICE
CERTIFICATE OF CORRECTION

PATENT NO.    : 5,771,903
DATED         : June 30, 1998
INVENTOR(S)   : Arne Jakobsson and Peter Forsell It is certified that error appears in the above-identified patent and that said Letters Patent is hereby corrected as shown below:

<u>Title page,</u>
Item [75], Inventors, please add the following inventor:
-- Peter Forsell --

Signed and Sealed this

Third Day of August, 2004

JON W. DUDAS
*Acting Director of the United States Patent and Trademark Office*